(12) United States Patent
Petisce (10) Patent No.: US 11,703,502 B2
(45) Date of Patent: Jul. 18, 2023

(54) VERTICAL FLOW ASSAY DEVICE FOR DETECTING GLUCOSE CONCENTRATION IN A FLUID SAMPLE

(71) Applicant: Becton, Dickinson and Company, Franklin Lakes, NJ (US)

(72) Inventor: James R. Petisce, Westford, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 980 days.

(21) Appl. No.: 16/477,440

(22) PCT Filed: Jan. 25, 2018

(86) PCT No.: PCT/US2018/015175
§ 371 (c)(1),
(2) Date: Jul. 11, 2019

(87) PCT Pub. No.: WO2018/140568
PCT Pub. Date: Aug. 2, 2018

(65) Prior Publication Data
US 2019/0383801 A1    Dec. 19, 2019

Related U.S. Application Data

(60) Provisional application No. 62/451,165, filed on Jan. 27, 2017.

(51) Int. Cl.
    *G01N 33/53*    (2006.01)
    *G01N 31/22*    (2006.01)
    *G01N 33/66*    (2006.01)

(52) U.S. Cl.
    CPC ......... *G01N 33/5302* (2013.01); *G01N 31/22* (2013.01); *G01N 33/66* (2013.01)

(58) Field of Classification Search
CPC .... G01N 33/5302; G01N 31/22; G01N 33/66; G01N 33/74; G01N 33/526; A61B 10/0051; A61B 10/007; A61B 10/0045
See application file for complete search history.

(56) References Cited

U.S. PATENT DOCUMENTS 4,066,403 A * 1/1978 Bruschi ................... C09B 23/02
                                                                                     435/12
4,144,306 A * 3/1979 Figueras ................ G01N 33/04
                                                                                     436/95

(Continued)

FOREIGN PATENT DOCUMENTS

JP     2004-535576 A    11/2004
JP     2010-515877 A    5/2010
(Continued)

OTHER PUBLICATIONS

Raphael C. Wong, "On-Site Oral-Fluid Drug Testing by Oratect", 2005, Forensic Science and Medicine: Drugs of Abuse: Body Fluid Testing, Edited by R. C. Wong and H. Y. Tse © Humana Press Inc., Totowa, NJ Chapter 9, pp. 145-159 (Year: 2005).*

(Continued)

*Primary Examiner* — Bao-Thuy L Nguyen
*Assistant Examiner* — Alexander Alexandrovic Volkov
(74) *Attorney, Agent, or Firm* — Dickinson Wright PLLC (57) ABSTRACT

A glycemic management related analyte detecting assay device (10) and method are provided for detecting and quantifying analyte concentrations in a fluid sample. The assay device includes an absorbent body containing an assay forming a detection zone for receiving a fluid test sample. The absorbent body is provided in a chamber of the device. The assay can detect one or more of a glycemic analyte selected from the group consisting of fasting plasma blood glucose, oral glucose, % glycated hemoglobin, and fasting insulin concentrations. In one embodiment, a container (Continued)

includes an absorbent body having a plurality of superimposed membranes (30, 32, 34, 36) where each membrane contains a reactant and a color indicator for detecting the presence of a selected analyte above a predetermined concentration in the fluid sample. The absorbent body and/or the assay include a color indicator that is able to provide a visual indication of the presence of one or more glycemic analytes present in the test sample.

25 Claims, 2 Drawing Sheets

(56) References Cited

U.S. PATENT DOCUMENTS

| | | | | |
|---|---|---|---|---|
| 4,337,065 | A | * | 6/1982 | Hiratsuka ........ G01N 33/54386 436/547 |
| 4,472,498 | A | * | 9/1984 | Masuda ............... G01N 33/521 435/805 |
| 4,587,102 | A | * | 5/1986 | Nagatomo ....... G01N 33/54386 435/805 |
| 4,806,311 | A | * | 2/1989 | Greenquist .......... G01N 33/525 435/7.8 |
| 4,806,312 | A | * | 2/1989 | Greenquist ...... G01N 33/54386 435/7.72 |
| 4,870,005 | A | * | 9/1989 | Akiyoshi ......... G01N 33/54386 435/805 |
| 4,897,347 | A | * | 1/1990 | Katsuyama .......... G01N 33/526 435/805 |
| 4,959,305 | A | * | 9/1990 | Woodrum ........ G01N 33/54386 435/7.7 |
| 5,250,443 | A | * | 10/1993 | Lindholm ........ G01N 33/54386 436/535 |
| 5,364,796 | A | * | 11/1994 | Blackwood ............ G01N 33/78 436/805 |
| 5,447,689 | A | * | 9/1995 | Gibboni ............... G01N 33/525 427/2.11 |
| 5,725,774 | A | * | 3/1998 | Neyer ..................... D04H 1/435 210/488 |
| 5,762,871 | A | | 6/1998 | Neyer |
| 8,802,427 | B2 | * | 8/2014 | Nazareth .................. C12Q 1/04 435/287.7 |
| 2002/0058330 | A1 | * | 5/2002 | Carroll ................. G01N 33/525 435/287.2 |
| 2002/0142291 | A1 | * | 10/2002 | Bauer .................. G01N 33/558 435/7.1 |
| 2003/0003522 | A1 | | 1/2003 | Goldman |
| 2004/0106215 | A1 | * | 6/2004 | Lehmann ......... G01N 33/54346 436/518 |
| 2004/0191119 | A1 | | 9/2004 | Zanzucchi et al. |
| 2006/0063267 | A1 | | 3/2006 | Lawrence et al. |
| 2009/0211345 | A1 | * | 8/2009 | Nahm ................ G01N 21/8483 73/61.55 |
| 2009/0311142 | A1 | | 12/2009 | Burgess-Cassler et al. |
| 2011/0144914 | A1 | | 6/2011 | Harrington et al. |
| 2011/0236991 | A1 | | 9/2011 | Lu et al. |
| 2013/0217054 | A1 | | 8/2013 | Huffstodt et al. |
| 2013/0331666 | A1 | | 12/2013 | Miller |
| 2016/0258943 | A1 | * | 9/2016 | Esfandiari ........ G01N 33/54386 |

FOREIGN PATENT DOCUMENTS

| | | |
|---|---|---|
| JP | 2010-207189 A | 9/2010 |
| JP | 2011-524526 A | 9/2011 |
| JP | 2015-064253 A | 4/2015 |
| WO | 2003/001964 A2 | 1/2003 |
| WO | 2008/049083 A2 | 4/2008 |

OTHER PUBLICATIONS

Can Zhang, Yan Zhang, and Shuo Wang, "Development of Multianalyte Flow-through and Lateral-Flow Assays Using Gold Particles and Horseradish Peroxidase as Tracers for the Rapid Determination of Carbaryl and Endosulfan in Agricultural Products", 2006, J. Agric. Food Chem., 54, 2502-2507 (Year: 2006).*

Tae-Gon Cha, Benjamin A. Baker, M. Dane Sauffer, Janette Salgado, David Jaroch, Jenna L. Rickus, D. Marshall Porterfield, and Jong Hyun Choi, "Optical Nanosensor Architecture for Cell-Signaling Molecules Using DNA Aptamer-Coated Carbon Nanotubes", 2011, ACS Nano, 5, 5, pp. 4236-4244 (Year: 2011).*

Young Kyoung Oh, Hyou-Arm Joung, Sanghyo Kim and Min-Gon Kim, "Vertical flow immunoassay (VFA) biosensor for a rapid one-step immunoassay", 2013, Lab Chip, 2013, 13, 768-772 (Year: 2013).*

Supplementary European Search Report dated Sep. 26, 2019, which issued in the counterpart European Patent Application No. 18744897.2.

International Search Report dated Apr. 17, 2018, which issued in the corresponding PCT Patent Application No. PCT/US2018/015175.

* cited by examiner

VERTICAL FLOW ASSAY DEVICE FOR DETECTING GLUCOSE CONCENTRATION IN A FLUID SAMPLE

This application claims priority to U.S. Provisional Patent Application No. 62/451,165 filed Jan. 27, 2017, which is hereby incorporated by reference in its entirety.

FIELD OF THE INVENTION

The present invention is directed to point of use assay for detecting at least one glycemic management related analyte concentration in a sample obtained from a patient. The invention is particularly directed to a vertical flow assay that can be used as the point of care by a technician or patient. In one embodiment, the assay is able to detect the presence of a plurality of glycemic analytes above a predetermined concentration in the sample at the same time.

BACKGROUND OF THE INVENTION

The diagnosis and monitoring of diabetes typically requires medical devices that include markers that are specific to glucose. Blood glucose management often relies on sampling blood where the samples are obtained by a clinician or other trained person. In other settings, the individual can draw a blood sample using a lancet or other device.

The blood sample can be applied to a test strip having a glucose detecting component or compound. A test strip can be inserted into an electronic glucose measuring device to determine glucose levels based on electrochemistry or color change from a chemical reaction on the test strip. The results then can be displayed on a display device. The test strips are generally considered a reliable glucose detection system at a reasonable cost. The test strips are able to provide glucose concentrations at the time of the sample so that the results may have a time variance to the actual changes in glucose concentrations.

While the prior devices have been found to be generally suitable for the intended purpose, there is a continuing need for improved methods and devices for detecting and quantifying glycemic analyte levels in a fluid sample. There is also a continuing need in the industry for improved testing devices that are able to utilize different types samples from different sources.

SUMMARY OF THE INVENTION

The present invention is directed to an assay device and method for use at a point of care such as in a physician's office. The invention is particularly directed to point of care device that is able to monitor and/or detect levels and concentrations of at least one glycemic management related analyte in a sample obtained from a patient. In one embodiment, the assay device is able to detect a plurality of selected analytes using a single sample and provide a positive indicator when the selected analytes are above a predetermined minimum threshold concentration.

One aspect of the invention is to provide an assay device and method that do not require refrigeration or a power source for use by the technician and is able to produce reliable results that can be repeated for monitoring and managing glucose levels in a patient. The assay device of the invention is compact and readily portable and easily used by the technician and/or patient. The assay device and method are able to detect at least one glycemic management related analyte and typically more than one analyte at the same time.

In one embodiment, the assay device is able to quickly detect the presence of at least one glycemic management related analyte selected from the group fasting blood plasma glucose, oral glucose level, % glycated hemoglobin, and fasting insulin concentrations.

The assay device is suitable for the point of care by a technician for producing reliable results in a short amount of time. The assay device and method are able to provide a visual reading or indicator of the presence of one or more of the glycemic analytes with a single sample without the use of specialized equipment.

The assay device in one embodiment relies on a vertical flow of a fluid sample and reagents by gravity through a testing material without the need for a power source or other equipment. The assay device can be self-contained device for possibly multiple use or preferably single use. The assay can include more than one type of assay for detecting glycemic management analyte concentrations in different fluid samples that may require different assay methods. In other embodiments, the assay can detect different glycemic management related analytes to provide an indication of the analytes above a threshold level or concentration in the sample. The detection of the analytes above a predetermined concentration in a sample can be by a visual indicator such a color indicator or chromogen that is visible to the user.

The device in one embodiment is a suitable container, vessel, or cartridge containing suitable reagents in an absorbent body where a fluid sample can pass through the absorbent body of the device by gravity in a vertical flow to a detection zone for detecting the presence of the tested analyte in the fluid sample. The detection zone can also include one or more reactants that can participate in the assay method and detect the presence of at least one glycemic management related analyte. A container can be coupled to the device can includes a suitable reactant for detecting and qualitatively measuring the analyte such as for example glucose levels in a sample. In other embodiments, the container that contains one or more of the assay components can be connected to the detection zone by a passage where the components are introduced by a flow to the absorbent body.

The absorbent body can include one or more detection agents arranged in the absorbent body where each detected analyte can be visualized and distinguished for each other. In one embodiment, a container can include a buffer for dispensing onto the absorbent body after the introduction of the test sample to disperse the test sample within the absorbent body.

In one embodiment of the invention, the device and method are able to detect at least one of fasting plasma blood glucose, oral glucose levels, % glycated hemoglobin, fasting insulin concentrations and combinations thereof, referred to herein as glycemic management related analytes. The vertical flow assay can detect at least one of these analytes and typically a plurality of analytes using a single sample. In one embodiment, the device and method are able to detect two or more of the analytes simultaneously from a single sample of bodily fluid and provide a visual indication of each detected analyte.

One feature is to provide an analyte assay device and method capable of detecting a threshold concentration level of one or more glycemic management related analytes, such as glucose, glycated hemoglobin and/or insulin concentrations in a liquid or fluid sample in a quick and convenient manner. The device includes an absorbent body having a detecting zone for receiving and stabilizing the fluid sample for detection of the analyte. The absorbent body is made of a material that can be provided in the detecting zone to receive the fluid sample by a downward flow and support the fluid sample to detect an analyte content at or above a predetermined concentration in the fluid sample. The assay components can be absorbed in the absorbent body until ready for use. In one embodiment, one or more of the assay components can be stored in a separate container or vessel that can deliver or introduce the assay components by gravity or capillary action to the detecting zone and the absorbent body for contacting the fluid sample where the analyte concentration in the fluid sample can be detected. The assay components stored in a container can be dispensed onto the absorbent body prior to or after the test sample is applied to the absorbent body. In other embodiments, two or more containers containing the same or different assay components can be coupled to the detecting device.

In one embodiment, the assay device and method are for detecting the presence of a minimum concentration of a plurality of analytes present in a single biological sample. The assay device can include a plurality of membranes where each membrane includes a different reagent for detecting a selected analyte. The membrane systems are arranged in a vertical manner so that the sample flows downward by gravity to or through each membrane without the need for an outside pressure source. Each membrane system is comprised of at least one polymeric layer.

In one embodiment of the invention, a vessel containing a buffer solution or an assay can be connected to the device. In another embodiment, the vessel is removable from the device and manufactured as a separate unit that can be connected to the detecting device for providing the buffer solution or assay component to the device either before or at the time of use.

Another aspect of the invention is to provide a method for detecting levels of a glycemic management related analyte in a fluid sample by providing an assay in the detecting device and supplying the fluid sample to the device. The method provides a detecting device having a detecting zone having an absorbent body for receiving and supporting the assay and the fluid sample. The fluid sample is delivered to the absorbent body within the detecting zone. The assay is retained in the detection zone for receiving the fluid sample by gravity where the analyte content can be determined. The absorbent body can be formed as a plurality of layers where each layer or membrane is able to detect the presence of a selected analyte. In one embodiment, the absorbent body includes a color indicator to visualize the presence of the selected analyte when the analyte is present in an amount above a predetermined concentration in the fluid sample. In another embodiment, the absorbent body can include more than one area or section containing a different assay and color indicator so that different analytes can be detected and provide a visualized indicator to the user of the presence or absence of a selected analyte.

The features of the invention and additional features will be apparent from the drawings and the following description of the device and method.

BRIEF DESCRIPTION OF THE DRAWINGS

The following is a brief description of the drawings in which.

DETAILED DESCRIPTION OF THE INVENTION

The present invention is directed to a glycemic management related analyte detecting device that is simple to use and can be used at the point of care. The detecting device does not require a power source for providing the results of the glucose detection and provides a visual indicator to the user by a vertical flow of the test sample by gravity through the device.

A method of providing a quick and simple assay of at least one glycemic management related analyte is provided by the use of the assay device. The method and device are able to detect the presence of at least one glycemic analyte and typically a plurality of glycemic analytes. The glycemic analyte can be, for example, fasting blood plasma glucose, oral glucose, percent glycated hemoglobin, and insulin. In one embodiment, the assay device can detect glycated albumin. In one embodiment, a biological sample can be deposited directly on the absorbent body of the device. In another embodiment, a sample can be collected in a vial or container and diluted with a suitable buffer solution. The sample is delivered to the device containing an absorbent body for assaying one or more analytes. The absorbent body can include assay components for assaying the selected analyte or a plurality of analytes. In one embodiment, the absorbent body includes a color indicator that reacts with the assay to provide a visual indication of each analyte to the user that the selected analyte is present in the sample at or above a predetermined concentration in the fluid sample.

Figure 1:
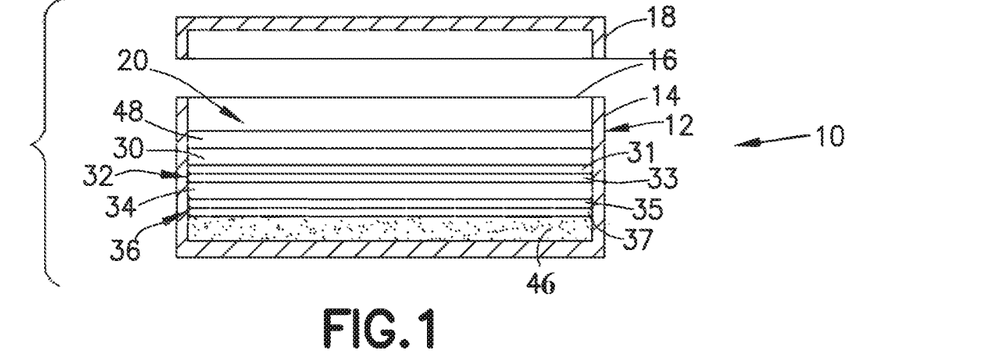
FIG. 1 is a side view in cross sectional of one embodiment of the device showing the container with the absorbent layers forming the absorbent body containing the assays for the selected analyte.

Referring to FIG. 1, one embodiment is the assay device 10 includes a housing 12 having a side wall 14 with an open end 16. The open end 16 has a dimension sufficient for introducing the test sample into the device for the assay and to observe the results of the assay. A cover 18 can provided to close the open end 16 before or after use.

An absorbent body 20 is included in a test zone within the housing 12 in the embodiment shown that is able to support the assay components and color indicator for the detected analyte. The absorbent body 20 can be a porous medium such as a membrane, paper or fibrous material or a hydrogel. In the embodiment shown, the assay components are contained in the absorbent body 20 or provided on the absorbent body that faces the open end 16. The assay components can be in a dry state on or in the absorbent body that can be re-hydrated by a solution or by a fluid test sample. The assay is provided in a suitable location in or on the absorbent body 20 so that depositing a test sample on the absorbent body 20 contacts the assay components to conduct the assay and activate the color indicator to provide a visible positive indication to the user to the presence of the target analyte. In the embodiment shown, the absorbent body includes a plurality of layers or membranes that can contain one or more reagents to reacting with a selected analyte and a color indicator or chromogen for detecting the presence of the selected analyte.

The absorbent body can be a suitable absorbent material that is able to retain the fluid sample and the assay reactants during the assay without interfering with the assay. The absorbent material can contain a dried reagent for detecting or participating in the detection and/or quantifying of the concentration of a glycemic management related analyte in the fluid sample. The absorbent material is typically a porous material that is able to absorb and support the fluid sample and receive the components from the container during the assay. The absorbent body is able to support a sufficient volume of the fluid sample in a layer for detecting concentrations of the glycemic management related analyte in the fluid sample. The resulting layer of the fluid sample can be sufficiently thin as needed to provide accurate detection of the analyte at or above a predetermined concentration in the fluid sample. The absorbent material as shown in the drawings is a thin porous material that covers the entire or substantially the entire bottom surface of the detection zone so that the amount of the free fluid sample is minimal. The absorbent material is able to absorb the fluid sample and distribute the fluid sample across the surface of the absorbent material for contact with the assay components from the container.

The absorbent body can be made of a suitable porous material that is able to absorb the fluid sample and uniformly distribute the fluid sample through the thickness of the absorbent material and across the width and length of the absorbent material. Suitable absorbent materials include a porous polymer substrate or fibrous material from polymer fibers or natural fibers such as a cellulose material.

Figure 2:
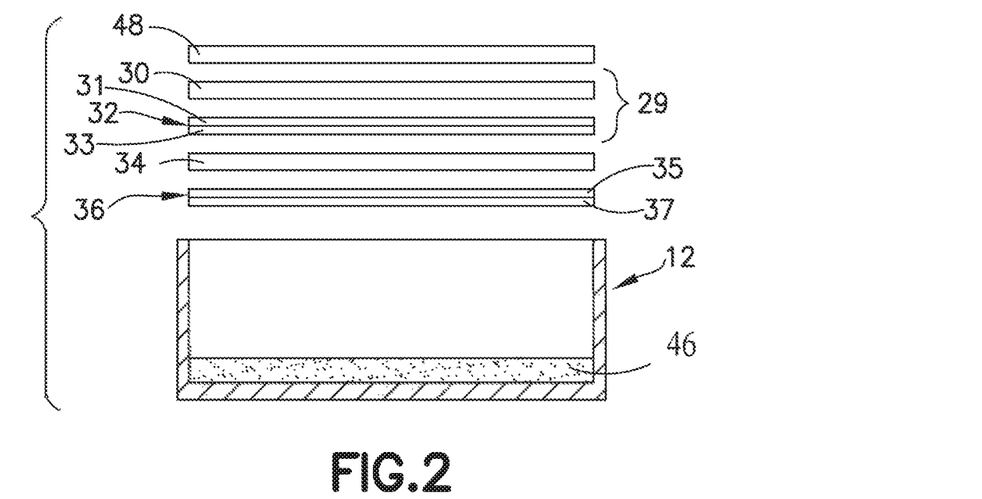
FIG. 2 is an exploded side view in cross section showing the membrane layers for detecting a selected analyte.
Figure 3:
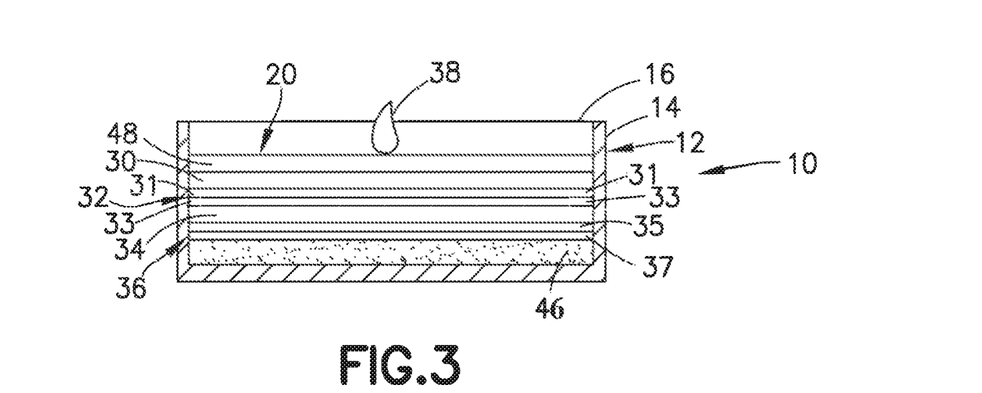
FIG. 3 is a side view in cross section showing the biological sample deposited on the absorbent body.

In one embodiment, the assay device includes a plurality of vertically arranged assay zones where each assay zone is configured for detecting the presence of a selected target glycemic management related analyte at or above a predetermined concentration in the fluid sample. The absorbent body can one or more membrane assays or membrane systems that include at least one and typically a plurality of porous membranes that are arranged or layered vertically on one another as shown in FIGS. 1-3 so that the fluid sample flows by gravity to each membrane. The membrane system can include more than one layer or membrane for reacting with a selected analyte and detecting the presence of the selected analyte. Each membrane system or membrane assay forms an assay zone for a selected target analyte. The membrane system contains at least one assay reactant and color indicator that are able to detect the presence of a selected analyte and provide a visual indication of the presence of the analyte when the concentration of the analyte in the sample is above a predetermined concentration in the fluid sample. The membrane system for a selected analyte can include a first layer or membrane that includes a reactant for reacting with the analyte to obtain compound or species as a reaction product. A second layer or membrane positioned below the first layer contains an indicator, such as a color indicator or chromogen, to detect the reaction product of the first layer thereby providing an indication of the presence of the selected glycemic analyte above a predetermined level. In another embodiment, a third layer or membrane can be provided below the second layer for detecting a second analyte that is different from the detected analyte in the second layer.

The membranes have a thickness that enables a color change that occurs in any one of the membranes to be visualized by the user through the top layer or membrane so that presence of one or more of the analytes can be detected and visualized. The membrane thickness can range from about 1 micron to about 10 microns and preferably in the range of about 2 microns to about 5 microns. The thickness of the membranes are formed to provide consistent thickness and to maintain the consistent and desired assay performance. Examples of membrane materials can be polyurethane, cellulose, cellulose derivatives, albumin, and synthetic non-woven materials. The color indicators of the different membrane assays are generally located in different areas relative to the visual field observed by the user so that each indicator in a selected membrane assay can be distinguished from the other detected analytes in another membrane assay.

The absorbent body in the embodiment shown has a plurality of layered membranes where each membrane is able to detect a predetermined concentration of at least one target analyte, such as glycated hemoglobin, insulin, and glucose. An absorbent pad 46 can be provided in the bottom of the housing 12 to absorb excess fluids or reagents to prevent leakage. The absorbent pad 46 can be made of the same material as the absorbent body or can be made of a different material. A top layer 48 of an absorbent material can be included to direct the fluid sample in a downward direction to the membranes. The membranes are arranged vertically so that a single sample can be deposited on the surface of the membranes to flow by gravity to or through each membrane to react with the reagent contained in the membranes. The reagents include at least one reagent for detecting the selected analyte and a color changing indicator or chromogen that produces a visual color change indicating the presence of the analyte above a predetermined concentration. Each reagent can be modified or tailored to provide a visual indication of the presence of a selected analyte when the analyte concentration is at or above predetermined threshold concentration level in the fluid sample and produces no visible color change when the concentration is below the threshold level. In one embodiment, the chromogens are selected so that minimal or no color change is visually detectable when the analyte concentration in the sample is below a predetermined concentration and provides a visible color change when the analyte concentration is above a predetermined concentration in the sample.

The assays can be modified to produce a color indication at desired concentration for the selected analyte. One method of determining the desired assay is to obtain a calibration plot for the selected analyte by measuring the absorbance of the chromogen as a function of the analyte concentration. From the plot, the chromogen absorbance at the selected clinical threshold analyte concentration is determined. The ability to observe the chromogen absorbance is adjusted and tuned by positioning visual attenuating membrane layer between the membrane layer containing the chromogen and the viewing position of the assay end user. Alternatively, the concentration of the chromogen is adjusted in the chromogen containing layer to allow visual detection by the end user at the selected clinical threshold analyte concentration.

Figure 4:
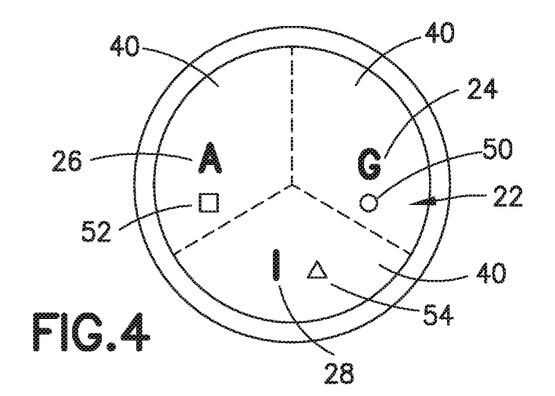
FIG. 4 is a top view showing the identification areas for each of the superimposed membrane layers containing the assay for a selected analyte.

In one embodiment, the membranes can be arranged so that the reagents and/or the color indicators are spaced laterally and not directly above or below one another to provide a clear view of the color indicators that provide the indication of the presence of a specific analyte as shown in FIG. 4. The color indicators can be provided on the membranes in a pattern or to provide indicia to identify the presence or absence of the target analyte. In other embodiments, the color indicators can provide different colors or visual effects to assist the user in distinguishing between the detected analytes.

In the embodiment shown in FIG. 4, the color indicators are arranged on or in each of the membranes or membrane systems so that indicia 22 formed by the color indicators are spaced laterally relative to each membrane or layer so that the color indicators can be visualized individually without interfering with the reading of another reagent and color indicator corresponding to the other assays. The membranes are sufficiently thin so that the color change in the membranes at the bottom of the array can be visualized through the upper membranes. In the embodiment shown in FIG. 4, the color indicators are formed in a pattern shown as a letter to indicate a positive indication of the detected analyte. In the embodiment shown, the letter G indicated by reference number 24 corresponds to the detection of glucose above a predetermined concentration, the letter A indicated by reference number 26 corresponds to the detected A1C above a predetermined concentration, and the letter I indicated by reference number 28 corresponds to the detected insulin above a predetermined concentration level in the sample. The letters are intended to be exemplary of the indicia to detect a selected analyte. Other geometric patterns or symbols such as a circle 50, a square 52, and a triangle 54 can be used as indications of the presence or absence of an analyte in the sample as shown in FIG. 4. The analytes can also be indicated by different color chromogens to distinguish between the detected analytes.

The assay in one embodiment can be for the testing of A1C to provide a visual indication of glycated hemoglobin and A1C level at or above a threshold level or concentration in the sample. The glycated hemoglobin and A1C threshold level or concentration is greater than about 6.5%, which is consistent with the 2018 American Diabetes Association's Standards of Care. If these Standards of Care change in the future, this threshold level or concentration in the sample can be adjusted accordingly. An example of an A1C assay can include a membrane having at least one reactant on or in the membrane that is able to provide a visual indication of the A1C level above a threshold level. In one embodiment shown in FIG. 2 a membrane assay or membrane system for the A1C assay 29 includes a first membrane system 30 includes a first layer or membrane containing a reagent capable of reacting with hemoglobin and a second layer or membrane containing a chromogen for indicating the presence of the target analyte. A whole blood sample can be supplied to the surface of the membrane system 30. A hemolyzing solution can be added onto the blood sample to lyse the sample and release the hemoglobin erythrocytes. The membrane 30 can contain a reagent and chromogen to react with the hemoglobin where the absorbance of hemoglobin can be visually observed at 570 nm for example. The chromogen can be positioned in a location where the color change can be visually detected when the hemoglobin in the sample is above a predetermined concentration. The amount of reagent contained in the membrane can be selected to provide a visual indication on the membrane of the amount of hemoglobin in the sample above a threshold concentration.

A second reaction solution, such as a protease, can then be added to the blood sample on the membrane system 30 of the absorbent body to release fructosylated dipeptides from the N-terminal hemoglobin β-chain. An example of a protease in N-(1-deoxyfructosyl)-hexapeptide. A second membrane 32 of the membrane system 30 of the assay 29 contains fructosyl peptide oxidase to release hydrogen peroxide in the presence of the sample. A chromogen in the presence of peroxidase on the membrane produces the color change to visually detect the presence and amount of hydrogen peroxide produced as an indication of the amount of glycated hemoglobin in the blood sample. In one embodiment, the peroxidase can be provided in a first layer or membrane 31 to produce the hydrogen peroxide and a second layer 33 can contain the chromogen to produce the color change. The chromogen and peroxidase can be modified to provide an indication of the hemoglobin at or above a threshold concentration. The chromogen and peroxidase can be contained in second membrane positioned below a first membrane containing the other reactants and can be arranged to produce a pattern or indicia showing positive measurement of the glycated hemoglobin concentration as in FIG. 4.

An example of a colorimetric method of determining hydrogen peroxide converts 4-nitrophenyl boronic acid or 4-nitrophenyl boronic acid pinol ester to 4-nitrophenol which can be measured at 400 nm in neutral or acidic media.

Total hemoglobin can be determined by the cyanide methemoglobin method using potassium cyanide to turn the released hemoglobin cyanide hemoglobin to produce a visible color indication. An example of the method is described in Van Kampen, E, Zilstra W, "Standardization of hemoglobinometry II" Clinica Chimca Acta, 1961, vol 6, 538-44. Glycated hemoglobin can be by the use of fructoslyated dipeptides from the N-terminal hemoglobin beta chain released by the protease. Hydrogen peroxide is produces that is further reacted with an indicator dye or dye system such as phenol red. The reaction produces an increased absorption at 610 nm as a function of an increase in concentration of hydrogen peroxide.

In the absorbent media, a membrane 34 is provided with an analyte detecting agent, such as an aptamer that is able to bind to insulin for the detection of insulin and to provide a visual indication of the insulin content in the sample. The nucleic acid aptamer is a synthetic ligand that is specific to insulin. An example of as suitable aptamer is disclosed in Cha et al., ACS Nano, 2011 May 24, 5(5), 4236-4244 which is incorporated by reference in its entirety. The nucleic acid aptamer has chromogen or fluorophore conjugated to the aptamer to detect insulin. In the presence of insulin, the aptamer reconfigures to a different shape or size producing a color change relative to the aptamer in the absence of insulin. The aptamer includes a chromogen such that when the aptamer binds with insulin, the chromogen undergoes a color change that can be visible. An example of a chromogen covalently bonded to the insulin binding aptamer is alizarin. In the embodiment shown, the aptamer is contained in a single membrane.

The aptamer with the chromogen is provided on a membrane layer of the absorbent media in a pattern that is spaced laterally from the chromogens or color indicators of the other membranes to the resulting pattern produced by the presence of insulin above a predetermined concentration in the sample can be visualized. Preferably, the aptamer is positioned in the membrane layer so that the color indicator or indicia does not overlap or obscure the visibility of the indicators of the other superimposed membranes that detect a different analyte as shown in FIG. 4. The chromogen concentration in a membrane or membrane system can be at least equal to the selected clinical threshold concentration of the analyte. The chromogen concentration can be modified to accommodate for the binding constant of the analyte to the chromogen or the reactivity of the analyte with the reagent which produces the indirect indicator that reacts with the chromogen.

The detected insulin concentration can be adjusted according to the requirements of an individual as there is no consensus among physicians of a threshold concentration of insulin. In one embodiment, the aptamer can be adjusted or modified to detect a threshold insulin concentration about 8.4 microunits/ml (mcU/ml).

A membrane system or membrane assay 36 can be superimposed with the other membranes of the absorbent body forming the absorbent media for detecting an amount of glucose in the sample. The reagents for detecting the presence of glucose above a threshold concentration in the sample can be any suitable assay that is able to produce a color change when the level of glucose in the sample is above a predetermined threshold concentration. The threshold glucose (fasting glucose concentration) is 126 mg/dL or greater. In one embodiment, the glucose assay can be a glucose oxidase in a first layer or membrane 35 of the membrane assay 36 that can react with the glucose in the sample to release hydrogen peroxide. The membrane assay 36 has a second layer or membrane 37 containing a chromogen that detects the hydrogen peroxide to produce a color change when the glucose in the sample is above a predetermined concentration in the fluid sample.

In the embodiment described, the membrane assays are shown having two layers. In other embodiments, the membrane assay can have a third layer containing reactant and/or an indicator for detecting the presence of a second analyte. Additional layers or membranes can be included to detect any desired number of analytes, such as the glycemic analytes.

As shown in FIG. 3, a test sample, such as a blood sample 38, is placed on the absorbent body 20 positioned in the test zone. A buffer solution can be added onto the test sample as a carrier to introduce the blood sample to each membrane layer of the membrane system. The test sample and buffer solution is then absorbed into the absorbent body 20 where the test sample reacts with the assay components. An additional amount of a buffer can be deposited onto the absorbent body 20 to disperse the test sample throughout the absorbent body as needed. The assay components are selected to provide a quick and simple assay and detection of the selected analyte.

The glucose assay can be any suitable assay capable of detecting glucose and/or quantifying glucose levels in the fluid sample. In a similar manner, the device and the detecting zone are selected to complement the glucose assay to provide an effective detecting system. For example, the glucose assay can be for fasting plasma blood glucose that can detect a glucose level in the plasma above or below a threshold or predetermined concentration. In other embodiments the glucose assay can be for an oral glucose challenge test to indicate a glucose concentration above or below a threshold concentration.

The glucose assay can be a suitable glucose assay capable of detecting and determining a level of glucose in the fluid sample. The assay can be based on the hexokinase method, glucose-oxidase method, glucose-reductase method and the like. HKL method using hemolyzate using hexokinase or GDL with hemolyzate using glucose dehydrogenase can also be used. In one embodiment, hexokinase/glucose-6-phosphate dehydrogenase is suitable where the hexokinase catalyzes the phosphorylation of glucose by ATP producing ADP and glucose-6-phosphate. The glucose-6-phosphate is oxidized to 6-phosphogluconate with reduction of NAD to NADH. Glucose can be reacted with glucose oxidase to produce hydrogen peroxide which is then reacted with an indicator dye or dye system such as phenol red. The reaction produces an increase absorption at 610 nm as a function of an increase in the hydrogen peroxide concentration.

The fluid sample can be any suitable sample capable of being used for detecting concentrations of the target analyte. The fluid sample can be whole blood, plasma, serum, serum, urine saliva, or other fluid sample capable of containing the glycemic related analytes in amounts that can be detected.

In one embodiment, a vessel containing the glucose assay is able to dispense the assay components to the detection or assay zone at the time of use. The vessel can be a flexible container that can be depressed by applying a manual or mechanical pressure to the outer surface of the container to dispense the contents. The container can have a suitable valve or seal that can open when a threshold external pressure is applied. In other embodiments, the device can include a piercing member that pierces a seal portion on the container to carry the contents to the detection zone. The piercing member can have an internal passage extending between the piercing end at the container and a suitable location above the absorbent material to deliver the contents to the absorbent material and the fluid sample. In other embodiments, the device can include an actuator that is able to apply an external pressure to the container to dispense the contents. In another embodiment, the container can include an integrally formed dispensing member such as a piston-like device that is capable of dispensing the glucose assay.

The absorbent body 20 can have a single assay component for detecting one type of analyte. The absorbent body 20 can be a single membrane or a plurality of membranes. In the embodiment shown in the drawings, the absorbent body 20 has a plurality of layers or membranes where each membrane has at least one section for assaying and identifying a different analyte. As shown in FIG. 4, the absorbent body has sections 40 where each section contains one or more assays in one or more of the membranes for detecting different analytes above a predetermined concentration in the sample. Each section includes a suitable indicator, such as a color indicator, that provides a visual indication of the presence of the analyte. As shown, each section 40 is provided with a visual indicator that is selective to a particular analyte that can be activated in the presence of the analyte. The presence of the analyte can be visualized by the user by a symbol, such as a dot or letter that appears after the assay and activation of the indicator.

Figure 5:
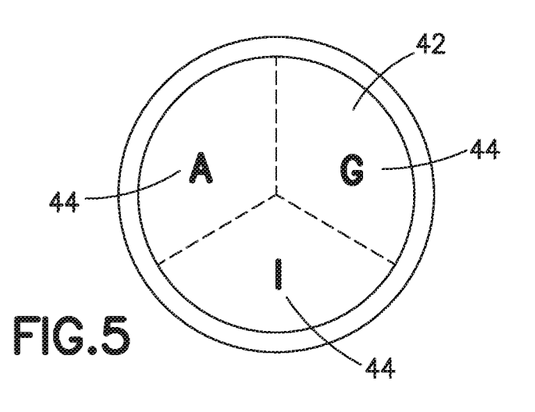
FIG. 5 is a top view of another embodiment where the membrane layers are positioned adjacent one another for detecting the presence of a selected analyte.

In an embodiment shown in FIG. 5, the membranes 42 are placed adjacent or next to each other. Each membrane 42 can include a different assay reactant and chromogen to identify a different analyte. As in the previous embodiment, color indicators can be provided in the respective assay to indicate the presence of the target analyte by suitable indicia 44.

Figure 6:
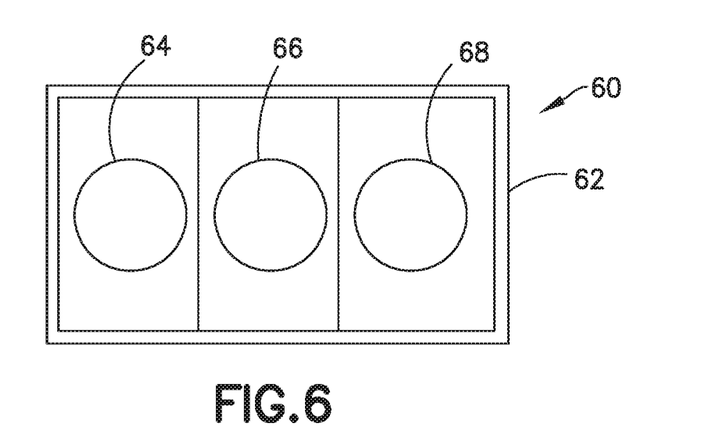
FIG. 6 is a top view of another embodiment where the membrane systems are arranged adjacent to one another in a linear array.

FIG. 6 is another embodiment of an assay device 60 including a container 62 supporting the absorbent body containing the assay components and chromogen. As shown in FIG. 6, the absorbent body is formed from three membranes 64, 66, and 68 to form three assay zones for a target analyte. As in the previous embodiment, each membrane includes the assay components and chromogen to detect a selected target analyte and provide a visual indication of the presence of the target analyte above a predetermined concentration in the fluid sample. The membranes each detect a different analyte as in the previous embodiments. The chromogen can produce a symbol or distinguishing color to identify the presence of the target analyte.

In another embodiment of the invention includes an assay and analyte detecting device 30 where the assay components are stored in a closed container until ready for use. The assay components are typically in a solution or a dried form that is reconstituted just prior to use. The assay components are deposited on an absorbent body before or after a test sample is deposited onto the absorbent body.

The device has a main body 12 for receiving reactants and a fluid sample. In the embodiment shown, the main body has a dimension for receiving a suitable volume of a fluid sample and the reactants or assay components for detecting glucose levels in the fluid sample. The absorbent body 20 typically has a dimension to cover the entire or substantially the entire bottom end of the detecting zone. In one embodiment, the absorbent body has a dimension with a sufficient surface area to enable the analyte in the fluid sample to be quantified either visually or by other detecting methods.

In one embodiment, a container or other suitable vessel can be provided that contains a suitable assay components for detecting a target analyte glucose concentration in the fluid sample. The container has an internal volume to contain an amount of the assay components for a fluid sample of a predetermined volume for the particular fluid sample. The container is closed to the environment to maintain the assay components in a stable condition until ready for use. The container has an outlet for dispensing one or more of the glucose assay components from the container to the detecting zone at the time of use. The outlet can be an opening or other passage such as a tube or to deliver the assay components at the time of use.

In use, the fluid sample is collected and deposited into the detection zone onto the absorbent body 20 where the fluid sample is retained and stabilized. The assay components can be then dispensed into the detection zone onto the absorbent body 20 containing the fluid sample where the assay components react with the fluid sample for detecting the presence of glucose in the fluid sample. The container can be is positioned in a vertical location relative to the detection zone so that the assay can flow downward into the detection zone without the use of pumps or a power source. The device provides a quick and reliable method for detecting and monitoring analyte levels in a fluid sample.

The container can be an integral part of the device or a separate unit that is attached and coupled to the body at the time of use. The body can be constructed to receive a single container for use in a single detection sequence. In other embodiments, two or more containers can be coupled to the body of the device for dispensing one or more assays. The containers can contain the same assay or different assays depending on the fluid sample. In further embodiments, the container can have two or more chambers where each chamber can contain the same or a different analyte assay.

The device of the invention can receive the fluid sample by direct contact with the absorbent body in the detecting zone. In other embodiments, the fluid sample can be supplied to a suitable port or inlet in the body of the device and carried to the detection zone. In the various embodiments of the invention, the fluid sample is introduced to the device in a manner where the fluid sample is able flow by gravity from the inlet port to the absorbent material in the detection zone without the need for a power source. In alternative embodiments, a manual mechanism can be provided to carry the fluid sample to the detecting zone.

The disclosure and drawings describe embodiments for providing a device for detecting and/or quantifying glucose concentrations in a fluid sample in a convenience and reliable manner. While certain embodiments have been described, various other embodiments of the device and the method for detecting glucose concentrations in a fluid sample can be made without departing from the scope of the disclosure.

It will be appreciated by those skilled in the art that changes may be made to the embodiments described herein without departing from the scope of the invention. It is particularly noted that the features of different embodiments and claims may be combined with each other as long as they do not contradict each other. All such changes and combinations are considered to be within the scope of the invention, which is defined by the appended claims and their equivalents.

The invention claimed is:

1. An assay device for detecting for the presence of at least one glycemic analyte in a fluid sample comprising:
   a test zone having an absorbent body positioned for receiving the fluid sample by a downward gravity flow,
   wherein said absorbent body includes a plurality of vertically arranged membrane assays where the fluid sample flows vertically through each membrane assay, each membrane assay includes an assay reactant for detecting a different glycemic analyte and a visual color indicator to produce a visual color indication of a selected analyte at or above a predetermined concentration in the fluid sample,
   wherein each of said membrane assays overlie one another.

2. The assay device of claim 1, wherein said assay reactant detects a glycemic analyte selected from the group consisting of fasting plasma blood glucose, oral glucose, percent glycated hemoglobin, and insulin concentration in the fluid sample.

3. The assay device of claim 1, wherein said assay reactant detects a fasting insulin concentration in the fluid sample.

4. The assay device of claim 1, wherein each membrane assay includes a first layer containing said assay reactant for detecting a different glycemic analyte and at least one second layer including said visual color indicator to produce the visual color indication of the selected analyte at or above a predetermined concentration in the fluid sample.

5. The assay device of claim 1, wherein said assay reactant is an aptamer configured for bonding with and detecting insulin, and where said aptamer contains a chromogen bonded to the aptamer for providing a color indicator in the presence of insulin.

6. The assay device of claim 1, wherein said membrane assays comprise a first layer including said assay reactant for reacting with a target glycemic analyte to produce a reaction product, and at least one second layer including said visual color indicator for detecting the presence of the target analyte above a predetermined concentration in the fluid sample.

7. The assay device of claim 6, further comprising a third membrane below said second membrane for detecting a second glycemic analyte.

8. The assay device of claim 1, wherein said color indicator in each membrane is visible through a top portion of the absorbent body.

9. The assay device of claim 1, wherein said color indicator of each membrane assay is spaced laterally from a visual color indicator of each other membrane assay.

10. The assay device of claim 1, wherein said visual color indicator of each membrane assay forms a selected pattern to identify the presence of a selected glycemic analyte in the fluid sample above a predetermined concentration in the fluid sample.

11. The assay device of claim 1, wherein
said absorbent body comprises a first membrane assay containing a reactant for detecting the presence of glucose in the fluid sample above a predetermined concentration and providing a visual color indicator of the presence of glucose, a second membrane assay containing a reactant for detecting the presence of % glycated hemoglobin above a predetermined concentration in the fluid sample and providing a visual color indicator of the presence of % glycated hemoglobin, and a third membrane assay containing a reactant for detecting the presence of insulin above a predetermined concentration in the fluid sample and providing a visual color indicator of the presence of insulin.

12. The assay device of claim 11, wherein said first membrane assay contains said visual color indicator in a first location, said second membrane assay contains said visual color indicator in a second location, and said third membrane assay contains said visual color indicator in a third location, where said locations of the color indicators are spaced laterally with respect to each other whereby indicia produced by each visual color indicator is visible through each membrane assay.

13. A method of detecting at least one analyte concentration in a fluid sample comprising the steps of:
introducing a fluid sample to the membrane assay device of claim 1, said membrane assay device having an absorbent body containing a plurality of locations containing at least one assay for detecting a glycemic analyte and for receiving and supporting the fluid sample, and
dispensing the fluid sample to the absorbent body and delivering the fluid sample to the locations by gravity into contact with at least one of the membrane assays of the absorbent material and detecting an analyte concentration in the fluid sample above a predetermined concentration in said fluid sample.

14. The method of claim 13, wherein said assay is capable of detecting glucose concentrations by a fasting plasma blood glucose method, oral glucose challenge test, percent glycated hemoglobin method, and fasting insulin concentration.

15. The method of claim 13, wherein
each of said membranes assays include a different reactant for detecting at least one selected from the group consisting of glucose, % glycated hemoglobin, and insulin in the fluid sample.

16. The method claim 13, wherein
said absorbent body includes a first membrane assay containing a reactant for detecting the presence of glucose in the fluid sample above a predetermined concentration and providing a visual color indicator, a second membrane assay containing a reactant for detecting the presence of % glycated hemoglobin above a predetermined concentration in the fluid sample and providing a visual color indicator, and a third membrane assay containing a reactant for detecting the presence of insulin above a predetermined concentration in the fluid sample and providing a visual color indicator.

17. The method of claim 16, wherein said first membrane assay contains said visual color indicator in a first location, said second membrane assay contains said visual color indicator in a second location, and said third membrane assay contains said visual color indicator in a third location, where said locations of the color indicators are spaced laterally with respect to each other whereby indicia produced by each visual color indicator is visible through each membrane assay.

18. The method of claim 17, wherein said indicia produced by a respective visual color indicator corresponds to the respective detected glycemic analyte.

19. An assay device for detecting for the presence of at least one glycemic analyte in a fluid sample comprising:
a test zone having an absorbent body positioned for receiving the fluid sample by a downward gravity flow, said absorbent body including a plurality of vertically arranged membrane assays where the fluid sample flows vertically downwardly through each membrane assay, each membrane assay includes a first layer with an assay reactant for detecting a different glycemic analyte and a second layer below said first layer having a color indicator for providing a visual indication of the presence of a selected first glycemic analyte, and a third layer below said second layer containing a visual color indicator for detecting a second glycemic analyte.

20. The assay device of claim 19, wherein each membrane assay is arranged whereby the fluid sample flows to each membrane assay by gravity.

21. The assay device of claim 19, wherein said assay reactant of said membrane assay is able to detect a glycemic analyte selected from the group consisting of glucose, insulin, and glycated hemoglobin.

22. The assay device of claim 19, wherein said assay reactant of said membrane assay is able to detect a fasting glucose concentration in the fluid sample.

23. The assay device of claim 19, wherein said color indicator for each membrane assay produces a color change when a respective glycemic analyte is detected at or above a predetermined concentration in the fluid sample.

24. The assay device of claim 19, wherein said color indicator of each membrane assay produces a different color.

25. The assay device of claim 19, wherein said color indicator of each membrane assay produces a different pattern or symbol.

* * * * *